(12) United States Patent
Jean et al.

(10) Patent No.: US 7,275,827 B2
(45) Date of Patent: Oct. 2, 2007

(54) SELECTIVE CORNEAL ABERROMETRY

(76) Inventors: Benedikt Jean, Sigmarszell (DE);
Thomas Bende, Mössingen (DE); Theo Oltrup, Tübingen (DE)

( * ) Notice: Subject to any disclaimer, the term of this patent is extended or adjusted under 35 U.S.C. 154(b) by 452 days.

(21) Appl. No.: 10/257,415

(22) PCT Filed: Apr. 11, 2001

(86) PCT No.: PCT/EP01/04142

§ 371 (c)(1),
(2), (4) Date: Dec. 16, 2003

(87) PCT Pub. No.: WO01/77739

PCT Pub. Date: Oct. 18, 2001

(65) Prior Publication Data

US 2004/0223118 A1    Nov. 11, 2004

Related U.S. Application Data

(60) Provisional application No. 60/196,532, filed on Apr. 11, 2000.

(51) Int. Cl.
*A61B 3/10* (2006.01)
(52) U.S. Cl. .................................................. 351/212
(58) Field of Classification Search ................ 351/212, 351/219, 221, 246, 211
See application file for complete search history.

(56) References Cited

U.S. PATENT DOCUMENTS 5,220,359 A    6/1993  Roffman ..................... 351/177
5,861,955 A *  1/1999  Gordon ...................... 356/511
5,929,970 A *  7/1999  Mihashi ..................... 351/205

OTHER PUBLICATIONS

Schwiegerling, Jim and Greivenkamp, John E., "Using Corneal Height Maps and Polynomial Decomposition to Determine Corneal Aberrations," Optometry and Vision Science, vol. 74 (11), Nov. 1997, pp. 906-916.

Greivenkamp, John E., et al., "Visual Acuity Modeling Using Optical Raytracing of Schematic Eyes," American Journal of Ophthalmology vol. 120 (2), 1995, pp. 227-240.

Schwiegerling, Jim and Snyder, Robert W., "Corneal Ablation Patterns to Correct for Spherical Aberration in Photorefractive Keratectomy," J Cateract Refract Surg, vol. 26, Feb. 2000, pp. 214-221.

Lapuerta, Pablo and Schein, Stanley J., "A Four-surface Schematic Eye of Macaque Monkey Obtained by an Optical Method," Vision Res., vol. 35 (16), 1995, pp. 2245-2254.

MacRae, Scott, et al., "Customized and Low Spherical Aberration Corneal Ablation Design," Journal of Refractive Surgery, vol. 15, Mar./Apr. 1999, (suppl), S246-S248.

* cited by examiner

*Primary Examiner*—Scott J. Sugarman
(74) *Attorney, Agent, or Firm*—Steven J. Hultquist; Intellectual Property/ Technology Law

(57) ABSTRACT

A method and system are disclosed for measuring and mapping the anterior surface topography of a cornea to determine corneal aberrations and an optimal ablation pattern for refractive and therapeutic surgery of the cornea. The invention stimulates a prospective ablation process with real-time visual feedback accurately portraying results of topographic surface alteration that would occur during an actual ablation procedure, thereby achieving minimal corneal aberrations and optimal image quality.

27 Claims, 5 Drawing Sheets

SELECTIVE CORNEAL ABERROMETRY

CROSS-REFERENCE TO RELATED APPLICATIONS

This application is filed under the provisions of 35 USC §371 and claims the priority of International Patent Application No. PCT/EP01/04142 filed Apr. 11, 2001, which in turn claims priority of U.S. Provisional Patent Application No. 60/196,532 filed Apr. 11, 2000.

BACKGROUND OF THE INVENTION

1. Field of the Invention

The present invention relates generally to surface profiling, and more specifically, to a method and system for measuring and mapping the anterior surface topography of a cornea to determine corneal aberrations and an optimal ablation pattern for refractive and therapeutic surgery of the cornea.

2. Description of the Related Art

Various methods have been developed to reshape the cornea of the human eye in order to correct for vision defects. Among these vision defects are nearsightedness (myopia), with the unaccommodated nominal focusing plane falling before the retina; farsightedness (hyperopia), with focusing plane beyond the retina; and the combination of defects known as astigmatism, in which the cornea has a toroidal shape and there is no plane of best focus. The most common methods to correct for these defects are spectacles and contact lenses (hard, soft and gas permeable types) that provide the correct amount of refractive power to shift the unaccommodated focusing plane to its optimum position on the retina. However, glasses are worn externally and are not infrequently perceived to be uncomfortable, inconvenient, or detracting from personal appearance.

Contact lenses are sometimes utilized when the use of glasses has been considered to be undesirable, mostly for cosmetic reasons. However, contact lenses entail problems of their own in terms of possible eye infection and the necessity for time consuming procedures required to maintain sterility and minimize contamination. More importantly, many people cannot tolerate the insertion of foreign objects on or in their eyes.

In response to a need for safe permanent correction of vision, without recourse to glasses or contact lenses, several major surgical methods for vision correction have evolved. For instance, radial keratotomy (RK), involves surgical incision of the cornea, with deep radial cuts outside the vision zone that cause a roughly predictable flattening of the cornea and a reduction in refractive power thereof, suitable for correcting low levels of myopia. Another procedure is corneal ablation with an excimer laser (photo refractive keratotomy (PRK)) which is achieved by selectively ablating corneal tissue from the anterior surface of the cornea or by varying the front surface curvature of the cornea.

Before corrective surgery, a patient usually has several diagnostic tests to determine the shape of the corneal surface. To date, measuring the corneal surface involves the use of aberrometric devices that generate an individual diagnostic set of data relating to the eye structure to determine an ablation pattern for subsequent adaptation to an appropriate laser delivery system. However, systems and methods used heretofore determine total aberrations of the optical system and introduce not only corneal aberrations but also aberrations relating to variable elements within the eye, such as the crystalline lens, accommodation of the lens, and vitreous structures. Thus, the measured dioptric values do not provide the option of differentiating aberrations caused by the variable elements from that of corneal aberrations originating on the anterior corneal surface. As such, a corrective ablation procedure for reshaping the cornea may not adequately compensate or may over-compensate due to aberration data from the undifferentiated variables.

Further, determining the topographic surface of the cornea with today's aberrometers does not provide sufficient data to measure the entire area of the cornea because generally the aberrometers utilize only around 100 measurement points with an accuracy of ±100 μm in the x and y plane. Considering that the x/y reference plane is centered about the pupilar margin, and a corneal surface is usually about 8.5 mm in diameter, there is not sufficient data to generate a topographic surface map with the necessary precession.

Accordingly, at the present time, a need exists in the art for a method and system that determine the topographic surface of the cornea with sufficient accuracy.

SUMMARY OF THE INVENTION

The present invention relates to a method and system for determining the surface topography of a cornea to accurately represent the topography of the corneal surface and provide guidance for permanent corneal reshaping that corrects for only corneal aberrations.

Additionally, the present invention relates to a system and method that provide a virtual image of the topographic surface of the cornea that may be combined with virtual components of the optical system to determine the extent of corneal ablation required to achieve a positive effect on the optical properties of the eye.

Further, the present invention relates to a system and method that provide simulation of a prospective ablation process with real-time visual feedback accurately portraying results of topographic surface alteration that would occur during an actual ablation procedure to achieve minimal corneal aberrations and optimal image quality.

Still further, the present invention relates to a system and method that provide an accurate determination of corneal aberrations that do not include aberrations caused by internal structures within the optical system, i.e., crystalline lens, aqueous and vitreous humor.

In one aspect, the present invention relates to a system for analyzing optical properties of a structure, the system comprising:

means to topographically measure a surface of the structure and produce a measured topography of the surface;

means to create a virtual surface corresponding to the measured topography of the surface;

means to calculate paths of generated light beams contacting the virtual surface; and means to analyze the calculated paths.

In another aspect, the present invention relates to a system for analyzing optical properties of a structure into which light waves enter through a surface of the structure, the system comprising:

means to topographically measure a surface of the structure and produce a measured topography of the surface;

means to create and display a virtual structure substantially corresponding to the structure;

means to create and display a virtual surface corresponding to the measured topography of the surface of the structure, wherein the virtual surface is combined with the virtual structure;

means to generate and display virtual light waves for passage through the virtual surface into the virtual structure;

means to calculate paths of the virtual light waves passing through the virtual surface; and means to analyze the calculated paths to determine refractive power of the virtual surface.

In still another aspect, the invention relates to a system for analyzing optical properties of a structure into which light waves enter through a surface of the structure, for resolution of the light waves to create a picture, the system comprising:

means to topographically measure a surface of the structure and produce a measured topography of the surface;

means to create and display a virtual structure substantially corresponding to the structure;

means to create and display a virtual surface corresponding to the measured topography of the surface of the structure, wherein the virtual surface is combined with the virtual structure;

means for altering the virtual surface;

means to generate and display virtual light waves for passage through the virtual surface into the virtual structure;

means to calculate paths of the virtual light waves passing through the virtual surface; and means to analyze the calculated paths to determine when the virtual surface has been sufficiently altered to provide a refractive power that shifts the virtual light waves to a position within the virtual structure for resolution of the virtual light waves.

In a further aspect, the invention relates to a method for analyzing optical properties of a structure into which light waves enters through a surface of the structure, the method comprising:

measuring topographically a surface of the structure to produce a measured topography of the surface;

creating and displaying a virtual structure substantially corresponding to the structure;

creating and displaying a virtual surface corresponding to the measured topography of the surface of the structure and combining the virtual surface with the virtual structure;

generating and displaying virtual light waves for passage through the virtual surface into the virtual structure;

calculating paths of the virtual light waves passing through the virtual surface; and analyzing the calculated paths to determine refractive power of the virtual surface.

A further aspect of the invention relates to a method for analyzing optical properties of a structure into which light waves enter through a surface of the structure, for resolution of the light waves to create a picture, the method comprising:

measuring topographically a surface of the structure to produce a measured topography of the surface;

creating and displaying a virtual structure substantially corresponding to the structure;

creating and displaying a virtual surface corresponding to the measured topography of the surface of the structure, wherein the virtual surface is combined with the virtual structure;

altering the topography of the virtual surface;

generating and displaying virtual light waves for passage through the altered virtual surface into the virtual structure;

calculating paths of the virtual light waves passing through the altered virtual surface; and analyzing the calculated paths to determine when the altered virtual surface has been altered sufficiently to provide a refractive power that shifts the virtual light waves to a position within the virtual structure for optimal resolution of the virtual light waves to form a picture.

In a still further aspect, the present invention relates to a method for analyzing optical properties of a structure, the method comprising:

measuring topographically a surface of the structure and producing a measured topography of the surface;

creating a virtual surface corresponding to the measured topography of the surface;

calculating paths of generated light beams contacting the virtual surface; and analyzing the calculated paths.

Therefore, the invention provides a method and a system that determine the topographic surface of a cornea without necessarily combining aberration data received from other structures within the optical system and that provide a virtual simulation model utilizing the determined topographic surface for simulating results of a prospective ablation procedure.

It is obvious that a visual display of the calculated surfaces, light beams or the like might be omitted as long as the necessary data are provided to a person using the method or the system according to this invention.

Obviously, this method and this system are not limited to measurements and ablation processes at an eye but may be used with any optical system focusing pictures in a body, which pictures are created by beams entering said body through a surface. Especially, this method and this system may be used if the body comprises an internal structure being optically active.

Other aspects, features and embodiments in the invention will be more fully apparent from the ensuing disclosure and appended claims.

DETAILED DESCRIPTION OF THE INVENTION, AND PREFERRED EMBODIMENTS THEREOF

Determining pre-operative corneal topographic abnormalities is a major determinant for ensuring predictability and stability of a subsequent refractive surgical procedure. The present invention is based on the discovery that determining and utilizing the corneal surface topography is sufficient to analyze the optical system's deficiencies and provide information on the predictability and stability of these surgical procedures. Moreover, the present method and system enable the simulation of an ablation procedure to determine an effective custom ablation pattern to produce a positive effect on the optical properties of the eye resulting in sufficient refractive power to shift an unaccommodated focusing plane to its optimum position on the retina for increased visual acuity.

As stated above, the human eye is an optical system characterized by aberrations of several types. A contributing factor to these aberrations is the fact that the human eye is not a rotationally symmetric optical system. Additionally, corneas are never perfectly spherical, and as such, it is important that the deviations therefrom be accurately and topographically pre-determined for effective refractive correction.

Corneal topography is a method of measuring and quantifying the shape and curvature of the corneal surface. Most topographic devices include a placido disc made up of multiple circles, which is back lit or projected onto the corneal surface. The resultant circular images are reflected and captured with a video camera and then digitized for subsequent display on a monitor. Using the mathematics of convex mirrors and mathematical algorithms, the image size is measured and quantified. Generally, any conventional corneal topography device may be utilized in the present invention to generate illuminated concentric rings that are projected onto the anterior corneal surface of a patient's eye. The emitted light rays are reflected off the patient's cornea and at least a portion of the reflected light rays are captured by a lens and focused onto an imagining system, such as the video camera.

In accordance with the present invention, a preferred topographic instrument is the Tubingen Colour Ellipsoid Topometer (C-Scan) commercially available from Technomed Technology, Germany, as described in U.S. Pat. No. 5,640,962, the contents of which are incorporated by reference herein, for all purposes. Specifically, the topographic instrument provides x, y and z data to form a 3-D elevation map by utilizing at least three distinguishable recognition marks within a projection pattern projected onto the cornea surface. The distinguishable markings are utilized for measuring the surface topography of the cornea and accomplished by a projection body which is illuminated, for example, by a white light source and has transparent, preferably ring shaped zones of different colors. In the alternative, it possible to provide an arrangement of differently colored light sources, for example in form of an array of diodes.

Preferably, a graphics processing unit is utilized to capture the reflected data to form an image representing the reflective surface which may be compared with a stored reference, or other known information, to identify any distortions in the captured image. The computer means measures the deflection of the light rings by the reflecting anterior corneal surface. Specifically, the distortion of light reflected through the ring pattern by the conditions that exist on the corneal surface is analyzed to determine the corneal topography and any deformation in the patient's cornea. The resulting data may be displayed as a corneal curvature map wherein different colors correspond to corneal power and curvature.

Figure 1:
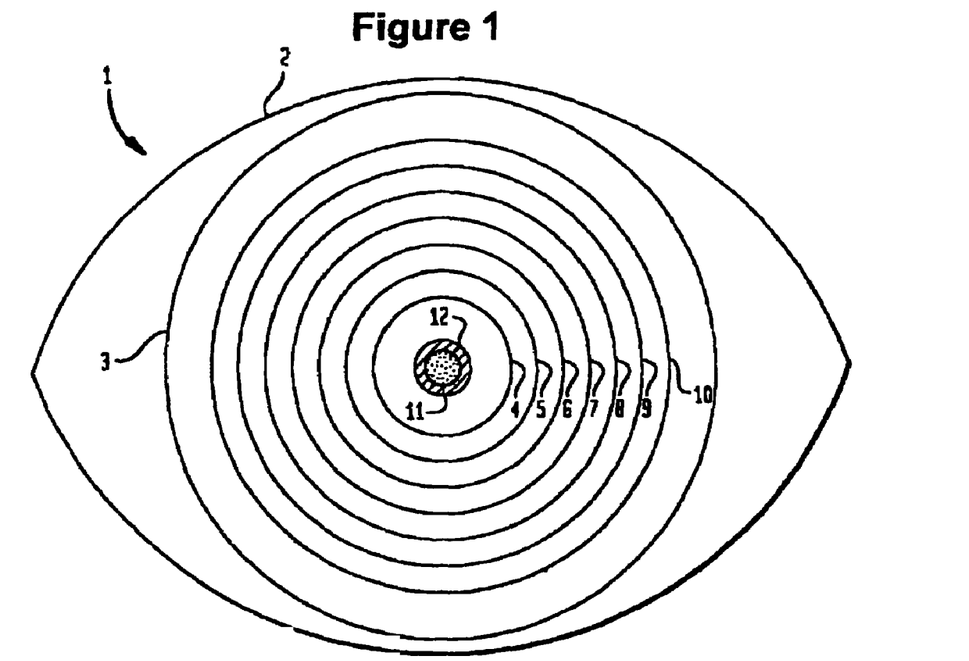
FIG. 1 shows the reflection pattern of a projection pattern comprised of several concentric rings projected on a spherical surface.

FIG. 1 shows schematically the image of an eye 1 of configuration 2 as registered by an image detection system of the above-described type. Depicted within the interior of the circumferential line 2 is the contour of the cornea 3. A placido disc is used to reflect rings of different colors onto the surface of the eye. Preferably, several reflection rings 4 to 10 are generated by the cone device shown in FIG. 3, wherein the rings are concentric to the Z-axis of the optical axis (camera-corneal apex). Located within the interior of these rings are two centering objects 11 and 12 that are described in more detail further below. The distance as well as the concentric and circular arrangement of the rings 4 to 10 correspond to the reflected image of a healthy cornea with spherical surface.

Figure 2:
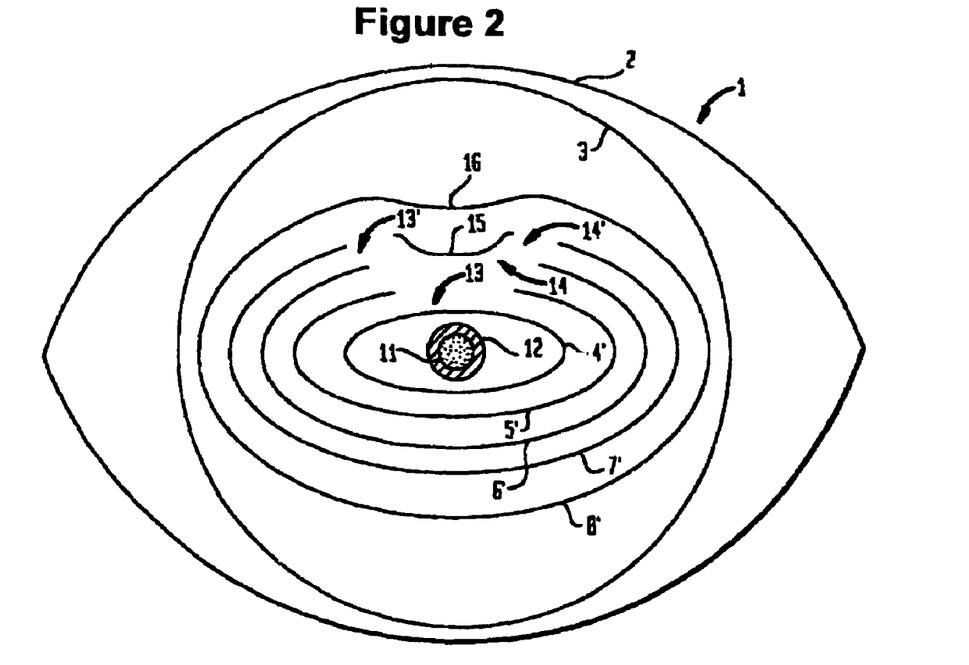
FIG. 2 shows an example of a comparable reflection pattern in the event of a cornea deviating from the spherical configuration.

In the case of astigmatism, the corresponding image of a deformed cornea is shown in FIG. 2. The structures 4' to 8' represent also a mirror reflection pattern of absolute concentric and circular projection rings. Their image is deformed by a non-spherical corneal surface. In part, the images 5' and 6' of the respective and originally closed projection rings have gaps 13, 14, 13' and 14' while other structures 7' and 8' show significant dents 15 and 16. In a normal black/white photograph, which cannot be illustrated in the drawing any differently, the zone 15 of the structure 7' cannot unequivocally be associated to a respective projection ring. This zone 15 could be associated to the projection rings as formed by the reflection rings 5, 6 or 7 of a healthy cornea (FIG. 1). Advantageously, because the rings 4 to 10 and the structures 4' to 8' are colored by a respective coloration of the projection pattern the zone 15 can be unequivocally associated with the correct projection ring.

Figure 3:
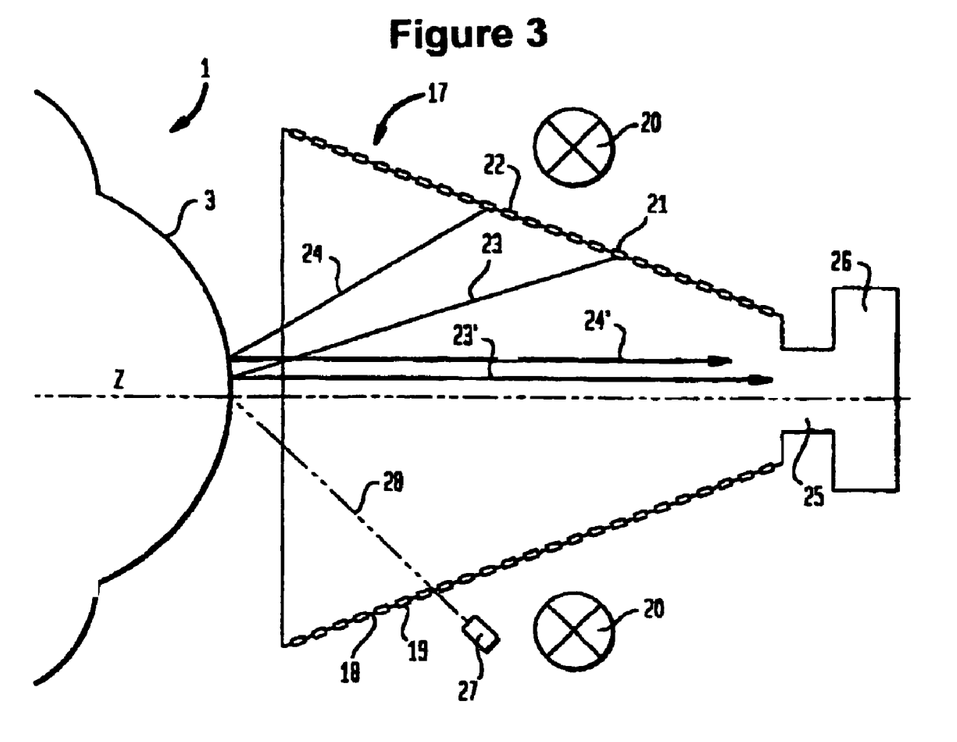
FIG. 3 shows a schematic illustration of an arrangement for carrying out the process according to the invention.
Figure 4:
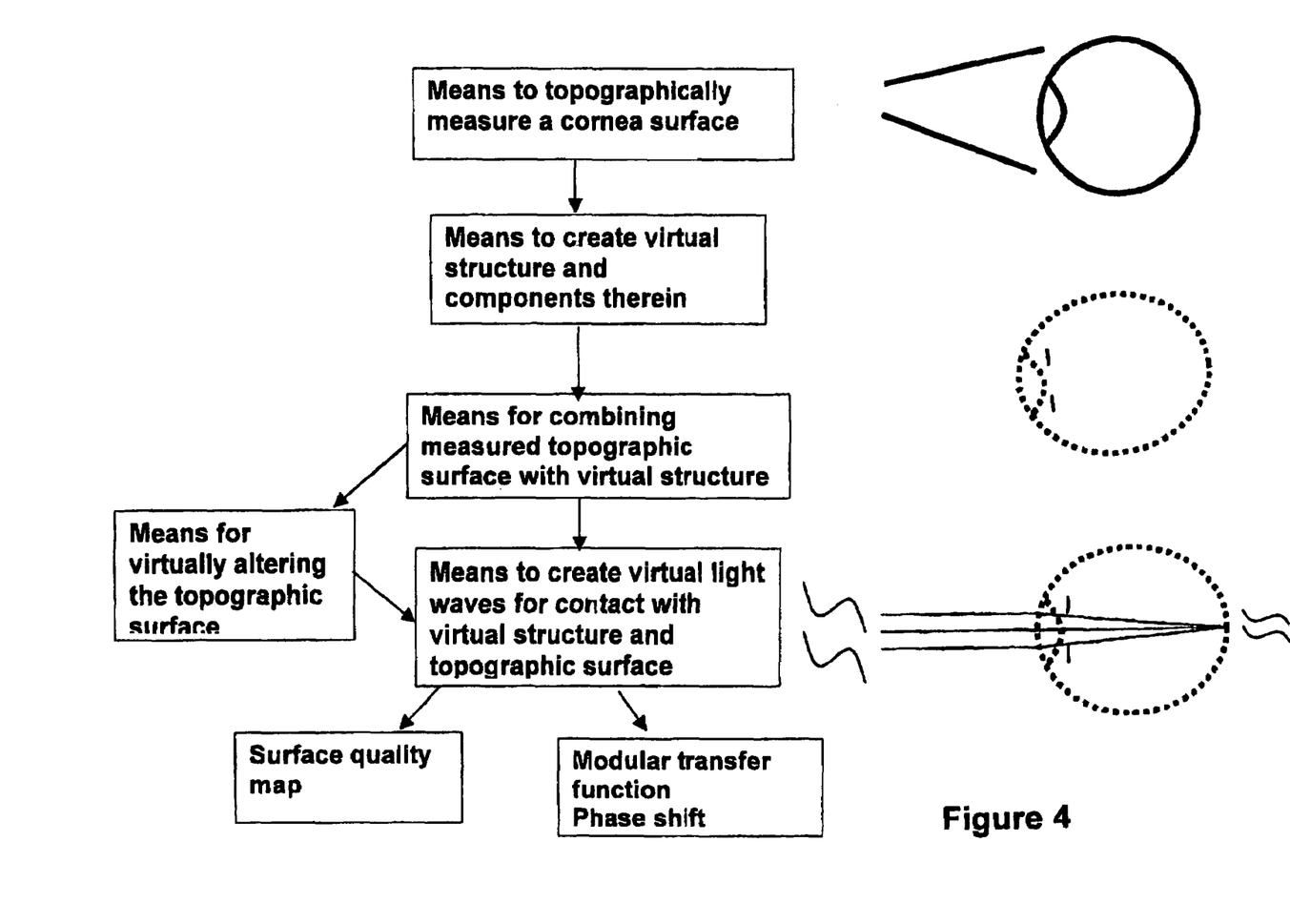
FIG. 4 is a block diagram of the system components of a preferred embodiment.

In a preferred embodiment, a projection body in the form of a hollow cone or a hollow ellipsoid with transparent rings, in particular color rings, is used in the side wall. FIG. 3 shows a schematic, sectional illustration of an arrangement for carrying out the measuring process according to the present invention. Positioned in front of the eye 1, with the arched cornea 3, is a projection body 17. The projection body 17 includes a cone-shaped hollow body, with a side wall 18 having ring-shaped, transparent and differently colored passages 19. The cone-shaped projection body 17 is illuminated from outside by a ring-shaped neon tube 20. The showing of two light beams emitting from differently colored ring-shaped passages 21 and 22 and symbolized by lines 23 and 34 illustrates the projection of the ring structures upon the cornea. The beams 23' and 24' reflected from the cornea 3 radiate through a pinhole diaphragm at the narrower end of the cone-shaped projection body 17 and form an image in an image detector 26. The Z-axis is formed, as stated above, by the prolongation of the axis of the image detection unit relative to the surface being measured.

It is important in the described process to attain a good adjustment of the surface, for example the corneal surface, relative to the image detection unit in Z-direction. The image-forming qualities of the entire arrangement depend significantly on this distance. The adjustment in direction of the Z-axis is preferably carried out through scanning-in of at least two centering objects in the projection pattern at a particular angle between their respective projection axes. The intersection of both projection axes yields the desired correct Z-position.

Centering objects 11 and 12 are scanned in at a certain angle between their projection axes in a plane which coincides with the Z-axis.

Alignment of objects 11 and 12 provides for good adjustment of the cornea surface relative to the image detection unit in the Z-direction and allows the determination of the Z-position of the corneal surface 3 and its evaluation. Laser beam 28 forms the centering object 11 e.g., on the cornea and laser unit 27 is arranged outside the projection body 17. The projection body includes a small aperture in its wall for passage of the laser beam 28 which then intersects the Z-axis in the desired point.

Preferably, the image detector 26 includes a video camera communicatively connected to a graphics processing unit. The reflection signals from the corneal surface are converted into electrical signals relative to their intensity and the signal may be automatically executed in the graphics processing unit having a display monitor. Preferably a digital camera is utilized because the electronic signals resulting from the charge coupled devices (CCD) are not turned into an analog signal, but instead remain in the form which they are recorded and transferred to the memory of the graphics processing unit as digital signals. The results may be outputted in the form of isoreflection lines which refer to those areas of the surface that have a same reflective power during the described measurement. Thus, the deviations from a standard of measurement are visible directly and without requiring any further interpretation of the measuring data.

To optimize the mapping of small corneal irregularities in corneal topography for subsequent use in corneal and refractive surgery, the data of small corneal irregularities are displayed in 3-D elevation maps.

Amplification is needed to display those irregularities e.g., scars, central island after PRK, amount of tissue removed. This may be achieved by subtracting a best fit sphere or in the alternative, a software program, commercially available from C-Scan, Technomed Technology, Germany, may be utilized. The program specifically utilizes the line of sight as a reference point (Z axis) combined with vector analysis and provides a multiplicity of point evaluations ranging from about 100 to 1000 to improve resolution. Further, this software tool is capable of compensating for errors which occur due to different image planes of different video topography pictures, such as before or after an ablation procedure.

The resolution of the corneal map cannot, in general, exceed the number of positions at which the data was acquired. It will be appreciated that increasing the resolution of the data can enhance the representation of the cornea scanning. To increase the resolution of the topographic surface of the cornea, a method described in U.S. Pat. No. 5,900,924 may be implemented, the contents of which are incorporated by reference herein for all purposes.

The generated high resolution topographic 3-D map of the corneal surface is displayed on a graphics processing unit. To determine optimal custom ablation of the measured topographic surface, a virtual structure, such as an eye structure is created on a geometric surface to form a manipulative three dimensional model of the eye and displayed on the graphics processing unit. The virtual eye may be created by any method known in the art including, photographing components of an ideal eye and texture mapping the photograph to develop a mathematical model of the eye. Further, an ideal virtual structure may be generated by a virtual reality drawing program such as, Optics Lab™, available from Science Lab Software, Carlsbad Calif. Additionally, a virtual retina is created to provide a surface for positioning a virtual image formed by convergence of light waves.

After creation of a virtual ideal eye structure, a virtual image or the image of the calculated topographic surface is connected or superimposed on the virtual ideal eye structure and displayed on the graphics processing unit. Additionally, internal structures of the eye structure may be included within the ideal virtual eye structure. For example, the patient's iris may be mathematical generated by a ray tracing virtual reality program or photographed for digital recreation on the displaying monitor. A digitized system is commercially available from Iridian Technologies, Moorestown, N.J.

Accordingly to the method and system of present invention, the optical properties of the topographical surface may be determined by the generation of virtual light waves that contact and/or pass through the virtual topographic surface into the interior of the ideal eye structure. A number of ray tracers software programs are currently available that convert a graphics processing unit or computer into an optics workstation and generate different beam platforms for design and analysis of optics system including, Optica™ which is commercially available form Wolfram Research, Inc., and Stellar™ from Stellar Software, Berkeley, Calif.

The generated virtual light waves may be in several forms, such as parallel beams, beams having varying intensity or color, patterns and frequencies.

Based upon data generated by the 3-D elevation map created by methods discussed above, a corneal surface segment which is defined by an area between at least four (4)measured points is tested for visual acuity. Fast ray tracing, using the high resolution 3-D elevation data in conjunction with Snell's law may be used to describe the diffraction of the incident virtual light waves and the resulting images on the virtual retina. Generally, every measurable surface irregularity causes a deviation for an incident light beam (optical aberration) which can be detected and quantified. A virtual light beam passing through the measured corneal surface, the iris and projected into a virtual retina results in an offset in relation to an ideal beam, passing through an optically ideal corneal surface. This offset can be processed quantitatively by projecting two points on the corneal surface whereby a mathematical peak to valley analysis leads to an index for the corneal resolution. The index values are determine for a multiplicity of corneal segments, preferably at least 100 segments, and more preferably between 250 and 1000 segments, to determine an index for the best corrected corneal visual acuity and deviations therefrom.

Figure 5:
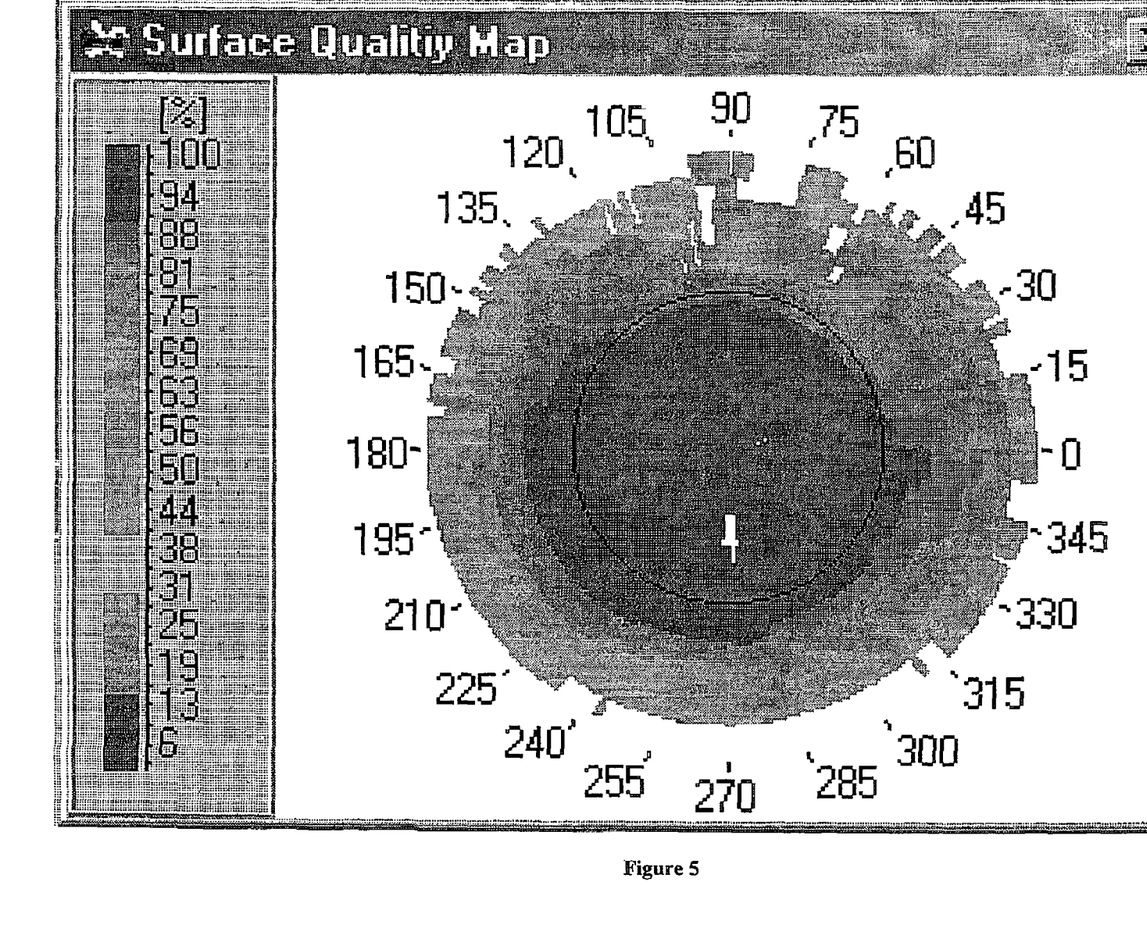
FIG. 5 shows a quality surface map according to the present invention.

Accordingly, the index values are correlated and projected back onto the corneal surface to generate a surface quality map. The surface quality map identifies the areas of the cornea with good or poor optical quality (lower or higher corneal aberration) and can display this information in both percentages and/or a color coded map as shown in FIG. 5. This surface quality map can also be used to determine the functional optical zones which show relative good optical quality and the map may be color coded according to visual acuity of more than 20/20.

Further, subtracting a best fitted sphere or asphere from the measured topographically surface will generate a difference map showing the amount and the location on the x and y plane of the cornea tissue that has to be removed during surgery to achieve a surface topography that improves visual acuity. Thus, the corneal surface is corrected by removing only tissue that will effect and improve visual acuity and avoiding ablation of corneal tissue that does not contribute to the improvement of optical properties.

Further, data relating to contrast sensitivity may be generated by varying the frequencies of the virtual light waves (sine or cosine wave) to calculate a projection that is comparable to known clinical contrast sensitivity charts. Thus, the high resolution 3-D topographic map may be further utilized as a projection screen whereon individual corneal segments are analyzed for a modular transfer function (MTF) and phase shift function (PSF) to quantitatively generate a optical transfer function. (Both the MTF and PSF may be created by the optics system Optica™ described above)

Heretofore, clinically used contrast sensitivity represented a combination of the contrast (modular transfer function) and sensitivity which is a function of the retina. Both parameters are measured in one clinical examination and subsequently included in a known vector vision chart. However, this is a subjective measurement and does not provide isolated information on the corneal surface unless a pre- and post-operative measurement is taken. This may still not always be effective because the patient must be extremely cooperative on both examinations to insure continuity in the alignment of the optical axis.

By the methods of the present invention the modular transfer function MTF appears as contrast and the phase shift function PSF indicates the shift of the image relative to the optical axis (Z-axis). Basically, a contrast map can be generated by using the 3-D elevation data of the video topometer and a simulated projection of a virtual sinus wave. Practically, this can be accomplished by using a point spread function and the projection of two points on the surface. Using the resulting point spread function g(k), the convolution $F_s(x)$ is calculated using the equation:

$$F_s(x) = \tfrac{1}{2} \Sigma_k (1 + \cos\,[\alpha\{x-k\}]) g(k)^6$$

with k=shift of spread function and x=local position on virtual retina.

The calculated projection of the sinus wave using real corneal elevation data can be analyzed for the contrast behavior C using the equation:

$$C = (I_{max} - I_{min})/(I_{max} + I_{min})^2$$

Where $I_{max}$=maximal light intensity (before passing cornea) and $I_{min}$=minimal light intensity (intensity on virtual retina).

Figure 6:
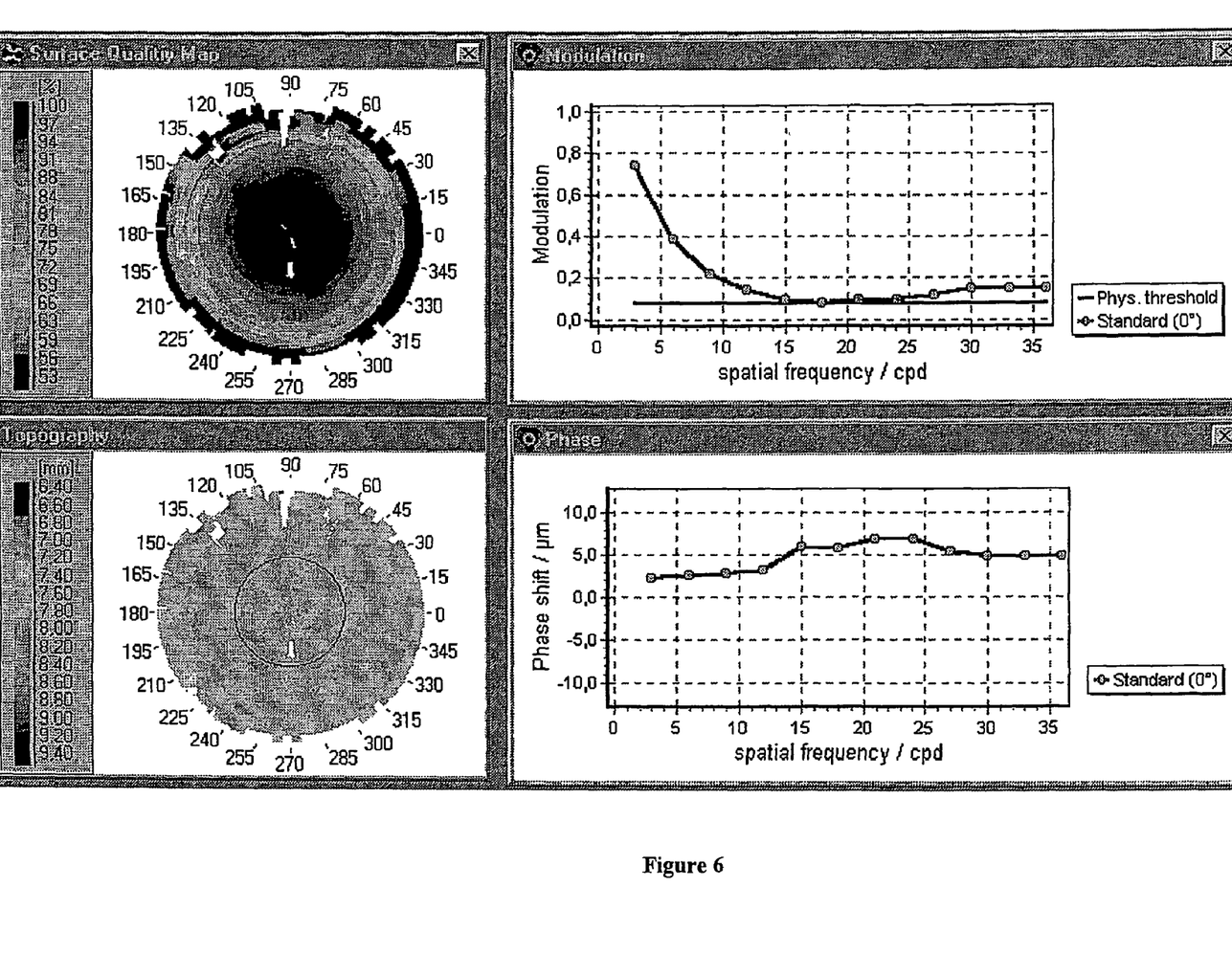
FIG. 6 shows a corneal aberration map according to the present invention.

A resulting graph or output, shown in FIG. 6, illustrates the contrast (modular transfer function) as a function of the sinus wave wherein visual acuity is given by the intersection of the contrast curve with the retinal sensitivity line.

The phase shift of the image is calculated to determine local tilt of the corneal surface for determining minimal amounts of decentration due to ablation procedures. Decentration acts as a local tilt and therefore leads to a shift of the image with regard to the optical axis. Different frequencies of sinus waves are transferred to the virtual retina, which is defined as the focal plane resulting from approximately three millimeters within the central area of the cornea. The phase shift occurs when the graph of a sin function A sin(ωt+φ) crosses the x axis and may be calculated by using a trigonometric identity for the sums of angles wherein the sum of a sine and a cosine curve is equivalent to a sine curve with a phase shift. A second graph shows the phase shift of the projected sinus wave relative to the optical axis as a function of the frequency. Both graphs, together with the included information, provides an optical transfer function (OTF). Further, the two graphs may be combined with the surface quality map, which provide the optical quality of each corneal point, to display the corneal optical aberrations as shown in FIG. 6.

EXAMPLE I

A standard 4.5D PRK myopia correction with an optical zone diameter of 6.5 mm, treated with an Apex plus (Summit, USA), was used to illustrate the obtained corneal aberration map (CAM), shown in FIG. 6, which combines the two graphs and surface quality map of FIG. 5. The aberration map is divided into four sub charts including, a radius map, surface quality map, contrast graph and phase shift graph. At the lower left of the CAM, the distribution of radii is shown which indicates a homogenous distribution. In the upper left of the CAM, the surface quality map shows a central dark gray area (normally a colored amp) which indicates, quantitatively, the optical aberration prevailing in a normal 20/20 eye having a diameter of 4.2 mm after the 4.5D PRK. The upper right graph shows "contrast" as a function of sinus wave frequencies and indicates that contrast decreases rapidly for lower frequencies. The horizontal line represent, in this graph, the physiological threshold and the intersection between the contrast curve and the physiological threshold correlates to the expected potential visual acuity for sinus wave structures. The phase shift graph in the lower right of the CAM shows the behavior of the phase shift as a function of frequencies and indicates the phase shift is almost constant.

The present map with the four charts can be used to provide information necessary to qualify the corneal aberration. While the corneal radius map is homogenous for the 6.5 mm diameter of the ablated optical zone, the surface quality map reduces the functional optical zone to 4.2 mm for a given amount of myopic correction. Thus, for daylight conditions, a functional optical zone of 4.2 mm in connection with a small pupil, provide high visual acuity and good contrast behavior. The information of the corneal aberration map can be used to guide a laser for customized ablation. Moreover, the corneal aberration map contains all the information to achieve minimal corneal aberration, and thus, optimal image quality.

Another embodiment of the present invention relates to the manipulation of the corneal surface to be performed by a virtual altering instrument created within the graphics processing unit or computer. For a virtual ablation procedure, a cut or removal of tissue caused by the virtual instrument is monitored by tracking the tip of the instrument and the virtual surface is reshaped to correspond to the virtual tissue removal. Subsequently, the visual acuity, as a result of each ablation cut, may be determined by testing the altered virtual topographic surface of the virtual cornea by methods described above. Accordingly, a pre-operative test may be performed to determine the optimal ablation procedure and to determine and achieve minimal corneal aberration.

In case of a medical application, in particular for determining the surface topography of the corneal surface of an eye, a measuring device which operates according the stated process, can be coupled directly onto the operating microscope to enable the surgeon to recognize corneal areas having a deviation from the desired geometry and to immediately render respective treatment.

That which is claimed is:

1. A system for analyzing optical properties of a structure into which light waves enter through a surface of the structure, the system comprising: means for topographically measuring a surface of the structure and producing a measured topography of the surface; means for creating a virtual structure substantially corresponding to the structure; means for creating a virtual surface corresponding to the measured topography of the surface of the structure, wherein the virtual surface is combined with the virtual structure; means for generating virtual light waves for passage through the virtual structure; means for calculating paths of the virtual light waves passing through the virtual surface; and means for analyzing the calculated paths to determine refractive power of the virtual surface.

2. The system according to claim 1, wherein the structure is an eye having a topographic surface.

3. The system according to claim 1 or 2, further comprising means for measuring an internal structure within the structure and means for creating a virtual internal structure substantially corresponding to the internal structure.

4. The system according to claim 3, wherein the internal structure is an iris.

5. The system according to claim 1, wherein said means for analyzing the calculated paths to determine the refractive power of the virtual surface, comprise means for creating a virtual focal area defining a virtual retina.

6. The system according to claim 5, wherein the calculated paths of the light waves merge at the focal area.

7. The system according to claim 1, wherein the light waves have varying intensity.

8. The system according to claim 7, wherein the means for analyzing the calculated paths comprise means for analyzing the phase shift of the beams of varying intensity, passing through the virtual surface, wherein the phase shift is analyzed with respect to an optical axis of the structure.

9. A system for analyzing optical properties of a structure into which light waves enter through a surface of the structure for resolution of the light waves to create a picture, the system comprising: means for topographically measuring a surface of the structure and producing a measured topography of the surface; means for creating a virtual structure substantially corresponding to the structure; means for creating a virtual surface corresponding to the measured topography of the surface of the structure, wherein the virtual surface is combined with the virtual structure; means for altering the virtual surface; means for generating virtual light waves for passage through the virtual surface into the virtual structure; means for calculating paths of the virtual light waves passing through the virtual surface; and means for analyzing the calculated paths to determine when the virtual surface has been sufficiently altered to provide a refractive power that shifts the virtual light waves to a position within the virtual structure for resolution of the virtual light waves.

10. The system according to claim 9, wherein the structure is an eye having a topographic surface.

11. The system according to claim 9, further comprising means for measuring an internal structure within the structure and means for creating a virtual internal structure substantially corresponding to the internal structure and being positioned in the virtual structure behind the virtual surface.

12. The system according to claim 11, wherein the internal structure is an iris.

13. The system according to claim 9, wherein said means for analyzing the calculated paths to determine when the virtual surface has been sufficiently altered, comprise means for creating a virtual focal area defining a virtual retina.

14. The system according to claim 13, wherein the calculated paths of the virtual light waves merge at the focal area.

15. The system according to claim 9, wherein the light waves have varying intensity.

16. The system according to claim 15, wherein the means for analyzing the calculated paths comprise means for analyzing the phase shift of the beams of varying intensity, passing through the virtual surface and the phase shift is analyzed with respect to an optical axis of the structure.

17. A system for analyzing optical properties of a structure, the system comprising: means for topographically measuring a surface of the structure and producing a measured topography of the surface; means for creating a virtual surface corresponding to the measured topography of the surface; means for calculating paths of generated light beams contacting the virtual surface; and means for analyzing the calculated paths.

18. A method for analyzing optical properties of a structure, the method comprising: measuring topographically a surface of the structure and producing a measured topography of the surface; creating a virtual surface corresponding to the measured topography of the surface; calculating paths of generated light beams contacting the virtual surface; and analyzing the calculated paths.

19. A method for analyzing optical properties of a structure into which light waves enter through a surface of the structure, the method comprising: measuring topographically a surface of the structure to produce a measured topography of the surface; creating a virtual structure substantially corresponding to the structure; creating a virtual surface corresponding to the measured topography of the surface of the structure and combining the virtual surface with the virtual structure; generating virtual light waves for passage through the virtual surface into the virtual structure; calculating paths of the virtual light waves passing through the virtual surface; and analyzing the calculated paths to determine refractive power of the virtual surface.

20. The method according to claim 19, wherein the structure is an eye having a topographic surface.

21. The method according to claim 19, further comprising measuring an internal structure within the structure and creating a virtual internal structure substantially corresponding to the internal structure and positioned in the virtual structure behind the virtual surface.

22. The method system according to claim 21, wherein the internal structure is an iris.

23. The method according to claim 19, creating a virtual focal area, i.e. a virtual retina.

24. The method according to claim 23, wherein the calculated paths of the virtual light waves merge at the focal area.

25. The method according to claim 19, wherein the light waves have varying intensity.

26. The method according to claim 25, wherein the means for analyzing the calculated paths comprise means for analyzing the phase shift of the beams of varying intensity, passing through the virtual surface wherein the phase shift is analyzed with respect to an optical axis of the structure.

27. A method for analyzing optical properties of a structure into which light waves enter through a surface of the structure for resolution of the light waves to create a picture, the method comprising: measuring topographically a surface of the structure to produce a measured topography of the surface; creating a virtual structure substantially corresponding to the structure; creating a virtual surface corresponding to the measured topography of the surface of the structure, wherein the virtual surface is combined with the virtual structure; altering the topography of the virtual surface; generating virtual light waves for passage through the altered virtual surface into the virtual structure; calculating paths of the virtual light waves passing through the altered virtual surface; and analyzing the calculated paths to determine when the altered virtual surface has been altered sufficiently to provide a refractive power that shifts the virtual light waves to a position within the virtual structure for resolution of the virtual light waves.

* * * * *